United States Patent
Bai

[11] Patent Number: 5,840,329
[45] Date of Patent: Nov. 24, 1998

[54] PULSATILE DRUG DELIVERY SYSTEM

[75] Inventor: Jane Pei-Fan Bai, Chadds Ford, Pa.

[73] Assignee: BioAdvances LLC, Philadelphia, Pa.

[21] Appl. No.: 857,105

[22] Filed: May 15, 1997

[51] Int. Cl.⁶ .............. A61K 9/26; A61K 9/58; A61K 9/60; A61K 9/62
[52] U.S. Cl. .......... 424/458; 424/457; 424/461; 424/462; 424/468; 424/494; 424/497; 424/469; 514/772.2; 514/772.3; 514/772.1; 514/777; 514/778; 514/779; 514/781; 514/782; 514/783; 514/786
[58] Field of Search ................... 424/451, 464, 424/490, 494, 496, 497, 498, 458, 461, 462, 469, 457, 468

[56] References Cited

U.S. PATENT DOCUMENTS

| | | | |
|---|---|---|---|
| 4,871,549 | 10/1989 | Ueda et al. | 424/494 |
| 5,283,065 | 2/1994 | Doyon et al. | 424/467 |
| 5,336,504 | 8/1994 | Geoghegan et al. | 424/462 |
| 5,364,620 | 11/1994 | Geoghegan et al. | 424/497 |
| 5,395,626 | 3/1995 | Kotwal et al. | 424/472 |
| 5,397,574 | 3/1995 | Chen | 424/451 |
| 5,445,829 | 8/1995 | Paradissis et al. | 424/480 |
| 5,472,708 | 12/1995 | Chen | 424/451 |
| 5,616,345 | 4/1997 | Geoghegan et al. | 424/497 |

*Primary Examiner*—Thurman K. Page
*Assistant Examiner*—James M. Spear
*Attorney, Agent, or Firm*—Synnestvedt & Lechner

[57] ABSTRACT

A pulsatile drug delivery system comprising of a plurality of particles is able to deliver drug in any desired patterns. A plurality of particles with multi-layer core capable of short-pulse release interlaced with long-duration release is designed for delivery of multi-agents simultaneously or sequentially, or single agent, according to a pre-programmed profile.

17 Claims, 2 Drawing Sheets

PULSATILE DRUG DELIVERY SYSTEM

FIELD OF THE INVENTION

This invention relates to a pre-programmed drug delivery system consisting of a plurality of particles which can deliver a therapeutic agent over a period of time. More specifically, the desired release profile is achieved by preparing a plurality of individual delivery units which release the active agent. The delivery system is able to deliver single agent, or multiple agents simultaneously or sequentially, in any desired pattern with predetermined timings of pulse release from, and predetermined pulse duration of, individual delivery units. The invention utilizes a novel hydrogel as the matrix material for the controlled release layer, a swelling agent for the rapid-release layer, and time-programmed coatings for the sequential dispensing of individual delivery units.

BACKGROUND OF THE INVENTION

In order to reduce dosing frequency and increase patient compliance, the prior art has disclosed controlled-release or time-release and pulsatile drug delivery systems. For instance, a Time-Controlled Explosion System (F.C.E.S.) is described in U.S. Pat. No. 4,871,549. In this system, drug is coated onto the seed along with the swelling agent, and the finished pellets are then coated with water-insoluble materials. Drug release is time-controlled by the breakage of the external water-insoluble membrane caused by the explosive swelling effect of swelling agents. The coating thickness of particles is increased to delay drug release. However, this system has the drawback of failing to release the drug if the swelling agents fail to rupture the water insoluble coating. Further, it lacks the flexibility of enabling various delivery patterns since the thickness of the coating determines the release of the drug.

To improve the disadvantages of T.C.E.S., a pulsatile drug delivery system has been described in U.S. Pat. No. 5,472,708, which uses a minor portion of water-soluble polymer and a permeability reducing agent added to the water-insoluble coating to guarantee drug release. Drug delivery is controlled by the rupture of the membrane. The system provides a pulsatile input of drug into the intestine with the timing of release regulated by the thickness of coating and the amount of water-soluble polymer. The duration of each pulse is the same among four groups of particles, creating four periods of fluctuation of plasma drug concentrations, which is indistinct from four separate administrations. The disadvantage of using water-soluble polymer to regulate time release is that once micro-sized patches of water polymers are dissolved, the active agent may start leaching out even before the coating is broken, leading to premature drug release, and inconsistency in drug efficacy. The system also suffers the disadvantage of T.C.E.S., by lacking flexibility in its release patterns.

Other pelletized controlled delivery systems are those described in U.S. Pat. No. 5,364,620, where a once-a-day formulation designed for diltiazem is described. The pellet consists of a core of diltiazem and a multiple layer membrane surrounding the core, like an onion. The membrane comprises a major proportion of a pharmaceutically acceptable film-forming, water insoluble synthetic polymer and a minor portion of film-forming, water soluble synthetic polymer. Drug release is determined by the number of membrane layers and the ratio of water soluble to water-insoluble polymer, and is a gradual process determined by the peeling of each layer in the onion-like structure. Once the water-soluble polymer of each membrane is dissolved, the membrane falls apart, resulting in drug release. In U.S. Pat. No. 5,336,504, a similar formulation for diltiazem is described for twice-a-day administration. With the release rate dependent on the erosion and dissolution of the membrane, the system provides a gradual release, but not the flexibility and capability of distinct sharp pulse release interlaced with prolonged controlled release.

In U.S. Pat. No. 5,283,065, a controlled release composition for spherical particles is described. Solid pharmaceutical diluents are used to form the granule matrix consisting of active medicaments. The granules are then compressed into a tablet, and the tablet is further coated with a film forming polymer. Drug delivery is controlled by disintegration of the granule matrix and not by an external coating. However, eighty to ninety percent of drug is released within 6 to 8 hours, thus requiring multiple administration of doses.

U.S. Pat. No. 5,395,626 describes multi-layer controlled release particles which consist of a core containing the active medicament, coated with a first layer of water soluble polymer, a second layer of controlled release barrier layer, a third layer of water soluble polymer, a fourth layer of active medicament, a fifth layer of water soluble polymer and a six layer of controlled release layer and a water soluble polymer layer. This system involves numerous tedious coatings using water-insoluble and water-soluble polymers as the separating barriers, not the drug-containing layers. The controlled release barrier consists of ethylcellulose, which is a semipermeable polymer. The system is only useful for drugs which are of highly water solubility.

U.S. Pat. No. 5,445,829 discloses an extended formulation comprising a mixture of immediate release particles and extended release particles, where the extended release is modified from the immediate release by an external coating consisting of dissolution-modifying plasticizers and film-forming agent. This system controls drug release using the diffusion-controlled membrane with a polymer plasticized with a plasticizer. This system only delivers an instant release overlapped by an extended release, and lacks the flexibility of delivering a slow-release followed by a rapid release and then by a slow release. Another disadvantage is that drug release starts immediately in the stomach, creating problems for an acid-sensitive drug.

In U.S. Pat. No. 5,397,574, a coating membrane of plasticized ethylcellulose is used for potassium chloride crystal, resulting in complete release within 8 hours after dosing. The disadvantage is that daily multiple administrations are required, and it lacks the flexibility of delivering various desired delivery patterns.

As more understandings of chronopharmacology are gained, delivery systems delivering only a zero-order extended release no longer meet the need of varying the plasma levels of drugs to synchronize with the circadian rhythm of body physiology and body reactions to a drug. There exists a need for a drug delivery system capable of dynamic, versatile, and reliable delivery patterns with the possibility of any desired release timing and duration, to reduce the fluctuation of plasma concentrations and to reduce side effects.

In general, the pharmaceutical industry has created controlled-release hydrogel matrices, to reduce dosing frequency, using a tablet formed by compressing a hydrogel polymer with a high compression pressure. The controlled-release mechanism is due to slow hydration of hydrogel polymer particles and slow diffusion of drug molecules through the swelling hydrated polymer particles. This does not allow a versatile delivery pattern because of the size of compressed tablet prohibits the number of layers being compressed into a tablet. Further, this practice is not be suitable for stress-labile and compression-labile molecules, such as an active medicament of proteinaceous nature.

Immunological tolerance is a basic protection mechanism through which self auto-immune attack on organs is suppressed. When the immune system reacts to self antigens present on the organs, immune attack on the organs begins and autoimmune diseases occur. Such instances include IDDM in which the immune system institutes an immune attack on the insulin-producing cells, resulting in a complete loss of cell functions and the onset of IDDM. Oral administration of autoantigens has been used to induce systemicimmunologic unresponsiveness to the antigens, which is termed as oral tolerance. More recently, several research laboratories have reported that a systemic tolerance can be induced by oral administration of autoantigens to arrest the systemic life-threatening immune attack on the organs and that oral administration of autoantigens can therefore prevent and delay the onset of autoimmune diseases. These therapeutic methods include administration of myelin basic protein to suppress multiple sclerosis, insulin to suppress juvenile diabetes, S-antigen to suppress uveoretinitis, alloantigen and MHC peptide to suppress rejection of transplantation, thyroglobulin to suppress thyroiditis, collagen to suppress arthritis, and acetylcholine receptor to suppress myasthenia gravis.

In view of the aforementioned disadvantages, there exists a pressing need for an oral pulsed delivery system suitable for continued, controlled release of autoantigens and chronotherapeutics. There also is a need for more reliable, flexible pelletized delivery systems which are capable of delivering single agents, or multiple agents simultaneously or sequentially, in any desired pattern, and which are useful for both protein/peptide drugs and non-protein drugs. There is a also a need for a delivery system capable of delivering drugs in versatile release patterns, including recurring sharp pulsed-doses interspersed with recurring prolonged, controlled pulsed-doses, or, if so desired, a delaying period, a drug-free interval, before any pulsed-doses, with a coating membrane that prevents premature release.

SUMMARY OF THE INVENTION

The present invention relates to a drug delivery system. More particularly, this invention relates to a drug delivery system which comprises a plurality of particles, enclosed in a tablet or capsule. The plurality of particles are divided into several delivery units, with each group having its own unique inner structured active core and specific external coating. These particles contain a polymer-blend hydrogel for the controlled-release matrix layer delivering controlled prolonged pulsed-doses, and swelling agent for the rapid release layer delivering recurring short, pulsed-doses. These particles contain an outer coating of a major portion of water-insoluble, water-permeable polymer, and a minor portion of water-insoluble, water-swellable polymer, and water-permeation adjusting agents for dispensing single or multiple precisely-timed pulsed-dose. The controlled-release layer and the swelling rapid release layer can each contain one or more active agents, which can be alike or different.

The object of the invention is to provide a versatile, controlled release drug delivery system which enables drug release in any desired pattern so as to synchronize with circadian biorhythm and to improve patient compliance with the convenience of once or twice daily therapy.

It is a further object of the present invention to provide a drug delivery system which can be programmed to release drug in a combined pattern of sharp, short pulsed-release dosages interlaced with long, controlled pulsed-release dosages to increase the efficacy of active medicament by once-a-day or twice-a-day administration.

It is a still further object of the present invention to develop a pelletized drug delivery system, which enables pulses of drug release in predetermined desired intervals of varying desired duration.

It is a still further object of the present invention to provide a method of preparing a controlled release hydrogel drug delivery system without the use of high compression pressure.

It is a still further object of the present invention to provide a versatile and flexible drug delivery system which can be flexibly manipulated to provide a particular delivery pattern.

It is a still further object of the present invention to provide a versatile drug delivery system which is applicable to both protein/peptide antigens and nonprotein/peptide active medicaments.

BRIEF DESCRIPTION OF THE DRAWINGS

FIG. 1a is a cross-section of a particle consisting of an inner core 2 and an external coating layer 1.

FIG. 1b is a cross-section of a particle which is a starch/sugar seed 3 coated with the controlled release layer 4 containing the active medicament distributed therein, followed by a swelling layer 5 containing the active medicament, and then by an external coating layer 1.

FIG. 1c is a cross-section of a particle which is a starch/sugar seed 3 coated with the first inner layer consisting of a controlled release layer 4 containing the active medicament distributed therein, followed by a swelling layer 6 without the active medicament, and then by an external coating layer 1.

FIG. 1d is a cross-section of a particle which is a starch/sugar seed 3 coated with the controlled release layer 4 containing active medicament distributed therein, followed by another controlled-release layer 7 containing a different active medicament distributed therein, followed by a swelling layer 6 without the active medicament, and then by an external coating layer 1.

DETAILED DESCRIPTION OF THE INVENTION

The invention discloses a pulsed drug delivery system comprising a plurality of particles, enclosed in a tablet or capsule, for any desired delivery patterns. The pulsed drug delivery system consists of a plurality of individual particles, with each unit having a unique structured inner core 1 and a specific external coating layer 2.

The external coating layer of the individual particles comprises of a major portion of water-insoluble, water-permeable polymer, and a minor portion of water-insoluble, water-swellable polymer and water permeation-adjusting agent.

The structured inner core of the individual particles contains one or more controlled release layers, with or without the active medicament, which may optionally be interposed with swelling layers, with or without the medicament. By judicious incorporation of the medicament in the various layers, the desired delivery pattern can be achieved.

The controlled release layer of the present invention comprises a controlled release matrix comprising a water-insoluble poly(acrylic acid) and a water-soluble polymer or monomer in a weight ratio ranging from 1:40 to 40:1, with the carbon-oxygen ratio of the polymer or monomer being less than or equal to 1.9:1, and the carbon-hydroxyl group ratio of the polymer or monomer being less than or equal to 5:1. Especially preferred are matrices having a weight ratio of the poly(acrylic acid) and water soluble polymer or monomer of 1:10 to 10:1. This matrix and its preparation are disclosed in co-pending provisional Application 60/031,334. The present invention is a further expansion and application of this matrix as a component of a drug delivery system.

In order to have the same type of pulsed-release recurring repeatedly, the individual particles will have the same structured internal core but different external coating layers. In order to have more than one type of pulsed-release dispensed simultaneously, the individual particles have the same external coating layer but a different structured internal core.

The manipulation of the structure of the internal core will produce a specific pattern of release.

Figure 1:
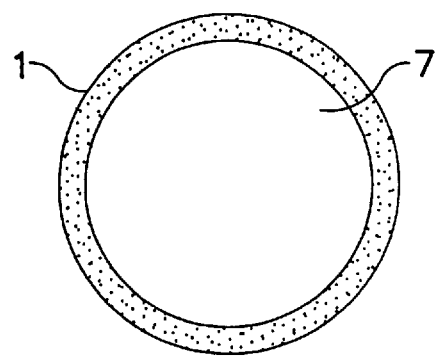
FIG. 1 shows the cross-sections of various embodiments of the present invention, each particle of the drug delivery system having a specific structured internal core and an external coating.
Figure 1:
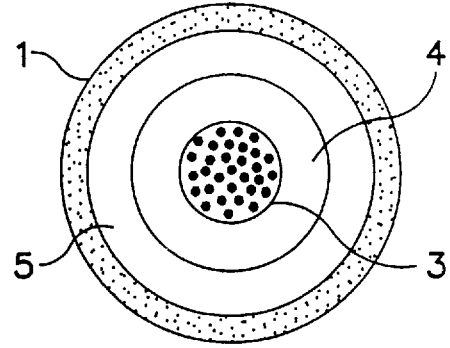
Figure 1:
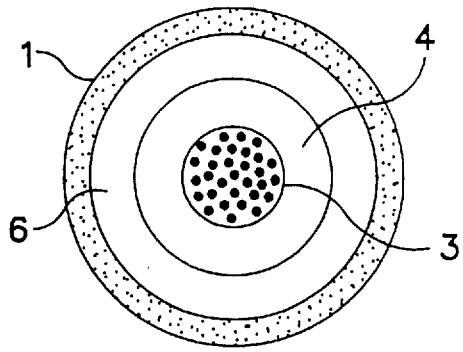
Figure 1:
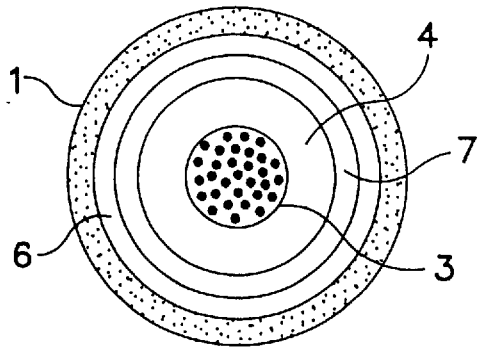

In the preferred embodiment of the present invention shown in FIG. 1b, the internal core of the particle comprises:
- a sugar/starch or cellulose seed 3
- a controlled release layer 4,
- surrounded by a swelling layer 5,
- with one or more active medicaments homogeneously dispersed in both layers; the particle then being coated with coating layer 1.

In this embodiment, the swelling layer 5 comprises the active medicament dispersed within the molecules of a swelling agent and the controlled release layer 4 consists of active medicament dispersed in the hydrogel controlled-release matrix. The pulsed-dose is delivered in two pulses with a short, sharp release of the dose of the active medicament from the swelling (rapid release) layer 5, followed by a sustained, controlled release of the dose of the active medicament. Multiple active agents can be dispersed separately or collectively in the individual layers so that different active agents are dispensed sequentially or simultaneously. The amount of each active medicament in the controlled release layer and in the swelling layer ranges from 5 to 95% and 95 to 5%, respectively.

In the further preferred embodiment shown in FIG. 1c, the internal core of each particle comprises
- a sugar/starch or cellulose seed or drug crystal 3
- a controlled release layer 4,
- followed by a swelling layer 6,
- with one or more active medicaments dispersed homogeneously in the controlled-release layer. The particle is coated with coating layer 1.

In this embodiment, the controlled release layer comprises the active medicament dispersed in the matrix material thereof, and the swelling layer consists of only swelling agent.

A further preferred embodiment of the present invention shown in FIG. 1d comprises a particle wherein the internal core comprises
- a sugar/starch or cellulose seed 3
- a controlled release layer 4,
- followed by a further controlled release hydrogel layer 7,
- followed by a swelling layer 6,
- with one or more active medicaments dispersed homogeneously only in the controlled release layers 4 and 7, and coated with a coating layer 1.

In this embodiment, the two controlled release layers each contain a different active medicament dispersed in the matrix material thereof, and the swelling layer consists of only swelling agent.

A still further preferred embodiment of the present invention is a particle wherein the internal core comprises
- a sugar/starch or cellulose seed 3
- a swelling layer 5,
- with one or more active medicaments homogeneously dispersed among the particles of swelling agents.

Groups of particles containing these internal distinct core can be combined in varying ways to deliver a predetermined release pattern in an once-a-day or twice-a-day or once-nightly dosage form.

The controlled release layer of the particles of the present invention comprises a matrix of a polymer blend of a water-insoluble poly(acrylic acid) polymer and a water soluble polymer or monomer, with the carbon-oxygen ratio of the water-soluble polymer or monomer being less than or equal to 1.9: 1. The poly(acrylic acid) utilized in the present invention can be any of the commercially available slightly cross-linked poly(acrylic acid) polymers. Polyacrylic acid polymers are commercially available from a number of sources. Highly preferred poly(acrylic acid) polymers are those available from BF Goodrich Specialty Chemicals, Cleveland, Ohio under the tradename Carbopol. Especially preferred are the pharmaceutical grade Carbopol 971P and 974P polymers of acrylic acid. These polymers form a gel in water when exposed to a pH environment above 4–6. Above their pK of 6 plus or minus 0.5, the carboxylate groups on the polymer backbone ionize, resulting in repulsion between the anions and further increasing the swelling of the polymer. These crosslinked polymers do not dissolve in water, but form colloidal gel dispersions. According to available product literature, these polymers possess an approximate molecular weight of about 3.5 billion, due to their cross-linked nature.

The Carbopol polymers, especially Carbopol 971P and 974P, are preferred for use in the matrix compositions of the present invention to control the release of the bioactive agent. The Carbopol matrix containing the bioactive agent can be compressed into tablets, optionally containing other excipients and active agents. Once such tablets are hydrated, discrete microgels of the matrix form a gelatinous layer on the tablet, which deters diffusion of drug molecules dispersed between polymer particles, thereby controlling drug release. Once completely hydrated, each microparticle of the matrix is a polymer web. The retention of the bioactive agent in the matrix web can be controlled by the firmness of the matrix formed by the addition of the particular water-soluble polymer or monomer to the matrix blend. Carbopol 971P and 974P have a low level of crosslinking and thus are preferred as the poly(acrylic acid) polymer in order to form a firm polymer blend with other polymers or monomers.

The water-soluble polymers and monomers utilizable in the present invention are those which are water-soluble and contain numerous carboxyl or hydroxyl groups so as to form blends with poly(acrylic acid). Examples of such water-soluble polymers include, but are not limited to, those such as collagen, pectin, hyaluronic acid, poly(vinyl pyridine), poly(vinylamine), poly(ethylene glycol), poly(methacrylamide), poly(vinyl acetate), poly(acrylamide), poly(vinyl alcohol), poly(hydroxyethyl methacrylate), hydroxypropyl cellulose, hydroxyethyl cellulose, sodium carboxymethyl cellulose, and poly(N-vinyl pyrrolidone), dextran, sodium alginate and propylene glycol alginate. Examples of such water-soluble monomers with capability to form extensive hydrogen bonding can also be mixed with swellable polymers. Those of pharmaceutical grade are especially desirable, including, but not limited to, those such as D-mannitol, xylitol, citric acid, fumaric acid, malic acid, and ascorbic acid. Preferred for use in the practice of this invention are the water-soluble polymers and monomers, sodium carboxymethyl cellulose, hydroxyethyl cellulose, propylene glycol alginate, xylitol, D-mannitol, dextran, sodium alginate and hydroxypropylcellulose.

The polymer blend is mixed using water or organic solvents of high polarity. Preferred water-insoluble poly(acrylic acid) polymers have molecular weights of 250,000 to about 3 billion. Especially preferred are the water-insoluble poly(acrylic acid) polymers which are Carbopol polymers with molecular weights of 260,000 to about 3 billion, such as Carbopol 974P and 971P (BF Goodrich, Cleveland, Ohio). In a preferred embodiment, the water-soluble polymers or monomers are those with a carbon-oxygen ratio being less than or equal to 1.9:1, and include, but not limited to, hydroxyethyl cellulose, hydroxypropyl cellulose, sodium carboxymethyl celluose, propylene glycol alginate, sodium alginate, dextran, D-mannitol, and xylitol.

Poly(acrylic acid), Carbopol 971P, sodium carboxymethyl cellulose, and hydroxyethyl cellulose are bioadhesive polymers. These polymers can thus provide a prolonged close contact with mucosal surface to increase absorption through mucosal tissues and interaction with mucosal immune systems.

The weight percentage of water-insoluble poly(acrylic acid) polymer and water-soluble polymer or monomer is 1:40 to 40:1.

Plasticizers are preferably included in the matrix material to optimize the diffusion of active medicament through the controlled-release layer for a desired release pattern. Said plasticizers include, but not limited to, sorbitol, triacetin, dimethyl phthalate, diethyl phthalate, dibutyl phthalate, dihexyl phthalate, butyl octyl phthalate, dibutyl sebacate, polyhyric alcohols, glycerides, castor oil, propylene glycol, glycerol triacetate, triethyl citrate, polyethylene glycol, glycerol, dioctyl azelate, epoxidized tallate, triisoctyl trimellitate, triisononyl trimellitate, sucrose acetate isobutyrate, epoxidized soybean oil, and acetylated monoglycerides. The weight % of plasticizers in the polymer blend, with the weight of the active medicament discounted, ranges from 0% to 35%, and is preferably about 1% to 25%.

When applicable, pharmacologically inert cationic compounds can be included in the controlled release layer, or are coated onto the sugar/starch or cellulose seed with pharmaceutical binders prior to the coating of the controlled release layer, so as to modify the rate of drug release. Such cationic compounds include, but are not limited to, lysine and arginine.

The swelling (rapid release) layer consists of a swelling agent and inert pharmaceutical excipients such as binders. Suitable swelling agents include, but are not limited to, low substituted hydroxypropylcellulose, cross-linked polyvinylpyrrolidone, cross-linked carboxymethylcellulose, pregelatinized starch, sodium starch glycolate, polyvinyl acetate, polyacrylic acid, acrylate-co-polymer, carboxymethylcellulose calcium, carboxymethylcellulose sodium, poly(hydroxyethyl-methacrylate), poly(methacrylic acid), poly(acrylamide), sodium starch glycolate, starch, poly(hydroxyalkyl methacrylate) with a molecular weight of 32,000 to 5,500,000, poly(electrolyte) complexes, poly(vinyl alcohol) with a low acetate residual, AquaKeep acrylate polymers with water absorbability of roughly 400 times its original weight, a mixture of poly(vinyl alcohol) and poly(N-vinyl-2-pyrrolidone), Good-rite poly(acrylic acid) with a molecular weight of 80,000 to 200,000, polyox polyethylene oxide polymers with a molecular weight of 100,000 to 5,000,000, polysaccharides (agar, acacia, karaya, tragacanth and algins), pectin with a molecular weight of 30,000 to 300,000, and polyoxybutylene-polyethylene block polymers.

Suitable pharmaceutical binders include, but are not limited to, agar, alginic acid, ethylcellulose, gelatin, guar gum, hydroxypropylmethyl cellulose, methylcellulose, polyvinylpyrrolidone, pregelatinized starch, tragacanth gum, microcrystalline cellulose.

The groups of particles can be further coated with individual specific external coatings so that the release of active medicament from the inner core is separated by sequential intervals. When applicable, a drug-free lag time can be instituted before the release of first dosage of the active medicament. This drug-free lag time is accomplished by delaying the first pulse-release.

The external coating layer is comprised of a major portion of water-insoluble, water-permeable polymer; a minor portion of water-insoluble, water-swellable polymer; and a water-permeation adjusting agent, either hydrophobic or hydrophilic in nature.

The external coating layer may be varied by changing the relative weight ratio of the major portion of water-insoluble, water-permeable polymer to the minor portion of water-insoluble, water-swellable polymer, by varying the amount of the water permeation-adjusting agent, and by varying the thickness of the coating. In the preferred embodiment, based on the total weight of water-insoluble, water-permeable and water-insoluble, water-swellable polymers, the weight percentage of the former ranges from 80% to 99.9%, and that of the latter is from 0.1% to 20%. In a highly preferred embodiment, the weight percentage of the former ranges 85% to 99.9% and that of the latter ranges from 0.1% to 15%.

Based on the total weight of three membrane components, the weight percentage of said water permeation-adjusting agent ranges from 0.01 to 15%. In the preferred embodiment, the weight percentage of said water permeation-adjusting agent ranges from 0.01% to 10%.

The water-insoluble, semi-permeable polymer allows the permeation of water into the particles to cause the swelling layer or the swelling, rapid release layer of the inner core to swell in volume several fold, causing the coating layer to rupture, and thus release the active medicament. The rupture of the coating layer can be further adjusted by varying the amounts of the water-insoluble, water-swellable polymer and the water-permeation adjusting agent, to ensure a definite, precise timing of pulsed release. The water-insoluble, water-swellable polymer swells upon contact with water and exerts stress and force horizontally on the layer, thereby weakening the layer and causing its rupture. Water permeation-adjusting agents, either hydrophilic or hydrophobic in nature, can increase or reduce water permeation for a further fine-tuning of the control of the pulsed-release. When the dose unit is in contact with an aqueous environment, the hydrophilic, swellable polymer of the external coating does not dissolve; therefore, the external coating layer of the present invention prevents premature leakage of the active medicament from the particle.

Suitable water-insoluble, water-permeable (semi-permeable) polymers for use in the present invention include, but are not limited to, cellulose acylate, cellulose acetate, cellulose diacylate, cellulose diacetate, cellulose triacylate, cellulose triacetate, mono-, di-, and tri-cellulose alkanylate, mono-, di- and tri-alkenylates, mono-, di- and tri-aroylates, cellulose trivalerate, cellulose trilaurate, cellulose tripalmitate, cellulose trioctanoate, cellulose tripropionate, cellulose diesters, cellulose disuccinate, cellulose dipalmitate, cellulose dioctanoate, cellulose dicarpylate, cellulose actate heptonate, cellulose valerate palmitate, cellulose acetate octonoate, cellulose propionate succinate, cellulose acetate valerate, cellulose acetaldehyde, dimethyl cellulose acetate, cellulose acetate ethylcarbamate, semipermeable polyamylsulfanes, semipermeable urethane, cellulose acetate methylcarbamate, cellulose dimethylaminoacetate, semipermeable sulfonated polystyrenes, semipermeable silicone rubbers, semipermeable styrenes, sulfonated polystyrenes, polyurethanes, polydiethylaminomethylstyrene, cellulose acetate methylcarbamate, ethylcellulose, shellac, polymethylstyrene, polyvinylacetate, seimpermeble (polysodium styrenesulfonate), and semipermeable poly (vinylbenzymtrimethyl ammonium chloride).

Suitable water insoluble, water-swellable polymers that swell upon contact with water and which are utilizable in the instant invention, include, but are not limited to, but not limited to, low substituted hydroxypropylcellulose, cross-linked polyvinylpyrrolidone, cross-linked carboxymethylcellulose, pregelatinized starch, sodium starch glycolate, polyvinyl acetate, polyacrylic acid polymers, Carbopol polymers with molecular weights of 260,000 to about 3 billion, Carbopol 974P and 971P, acrylate-co-polymer, carboxymethylcellulose calcium, carboxymethylcellulose sodium, poly(hydroxyethyl-methacrylate), poly(methacrylic acid), poly(acrylamide), sodium starch glycolate, starch, poly(hydroxyalkyl methacrylate) with a molecular weight of 32,000 to 5,500,000, poly(electrolyte) complexes, poly(vinyl alcohol) with a low acetate residual, AquaKeep acrylate polymers with water absorbability of roughly 400 times its original weight, a mixture of poly(vinyl alcohol) and poly(N-vinyl-2-pyrrolidone), Good-rite poly(acrylic acid) with a molecular weight of 80,000 to 200,000, Polyox polyethylene oxide polymers with a molecular weight of 100,000 to 5,000,000, polysaccharides (agar, acacia, karaya, tragacanth and algins), and polyoxybutylene-polyethylene block polymers.

Typical water permeation-adjusting agents, either hydrophilic or hydrophobic in nature, for use in the present invention can be selected from any of the pharmaceutical excipients compatible with the coating membrane polymers which are well-known in the art. Hydrophobic water permeation-adjusting agents increase the hydrophobicity of the coating membrane, making water less likely to permeate through said membrane or to wet said membrane and thus increase the time for said membrane to break. Hydrophilic water permeation-adjusting agents increase hydrophilicity of said membrane, and through an opposite mechanism reduce the time for said membrane to break. Such hydrophobic water permeation-adjusting agents include, but not limited to, fatty acids, metal salts of fatty acids and talc.

The combination of various types of pulsed-release to form various delivery patterns is exemplified by the following delivery systems which are briefly described below.

An exemplary drug delivery systems can consist of three groups of particles enclosed in an enteric-coated tablet or capsule, as follows:

Group a: 10–60% of the particles contain an inner controlled release layer surrounded by a swelling (rapid release) layer, with both layers containing an active medicament, and then by an external coating layer which allows the pulsed-release to begin once the particles are released from the tablet or capsule; and Group b: 40–90% of the particles contain an inner controlled release layer with active medicament, surrounded by a swelling layer without active medicament, and then by an external coating layer which allows the pulsed-release of the active medicament to begin 12 hours after the particles are released from the tablet or capsule. Alternatively, there may be two groups of these particles so that one group releases one-half of the active medicament within 18 hours after administration, and the other one-half of the active medicament is released within 24 hours of administration. This results in lag times for the two groups of particles with the same inner core of 12 and 18 hours.

Figure 2:
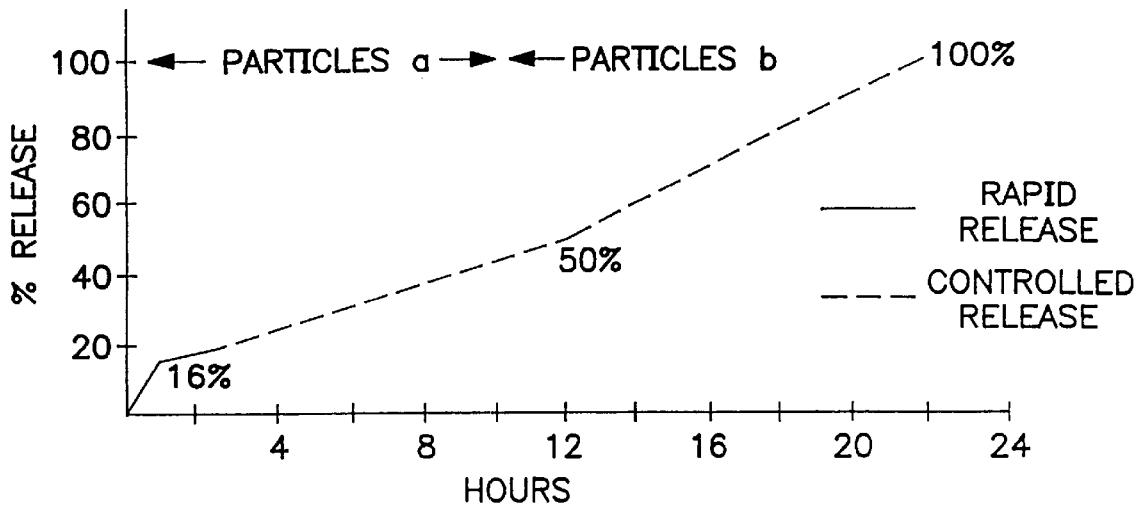
FIG. 2 is a graph showing the release of nifedipine from a drug delivery system consisting of 16% released from particles of group a between hour 0.5 and 1, and 34% dose released from particles of group a between hours 1–12 and 50% dose released from particles of group b between hours 13–22 (See Example 6).

FIG. 2 is a graph showing release rate of an active medicament using the above-described delivery system.

A further example of a drug delivery system in accordance with the present invention consists of three groups of particles enclosed in an enteric-coated tablet or capsule, as follows:

Group c: 10–60% of said particles comprise an inner controlled release layer containing the active medicament, which is surrounded by a swelling layer and then by an external coating with the external coating allowing the pulsed-release to begin once the particles are released from the tablet or capsule;

Group d: 10–40% of said particles comprise an inner controlled release layer containing with active medicament, which is surrounded by a swelling layer and then by an external coating with the external coating layer allowing the pulsed-release of the active medicament to begin 8 hours after the particles are released from the tablet or capsule; and Group e: 20–40% of said particles comprise an inner controlled release layer containing with active medicament, which is surrounded by a swelling layer and then by an external coating layer with the external coating layer allowing the pulsed-release of the active medicament to begin 16 hours after the particles are released from the tablet or capsule.

Figure 3:
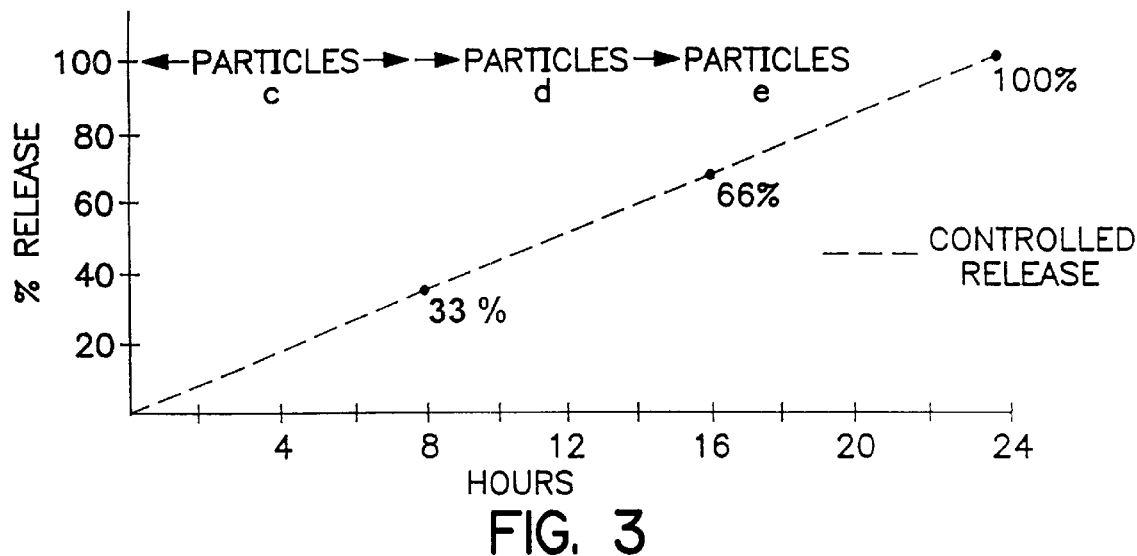
FIG. 3 is a graph showing the release of potassium chloride from a drug delivery system consisting of 33% of the dose released from particles of group c between hour 0–8 hours, 33% dose released from particles of group d between hours 9–16, and 33% dose released from in particles of group e between hours 17–24 (See Example 7).

FIG. 3 is a graph showing the release rate of an active medicament using the above-described delivery system.

A further drug delivery system in accordance with the instant invention comprises of three groups of particles in an enteric-coated dosage form, tablet or capsule, as follows:

Group f: 10–40% of the particles comprise an inner controlled release layer which contains the active medicament, surrounded by a swelling layer without active medicament, and then by an external coating layer which allows release of the active medicament to begin immediately once the particles are released from the tablet or capsule;

Group g: 20–80% of said particles comprise an inner controlled release layer, surrounded by a swelling rapid-release layer, with both layers containing the active medicament, and then by an external coating layer which allows release of the active medicament to begin 4 hours after the particles are released from the tablet or capsule; and Group h: 20–40% of said particles comprise an inner controlled release layer containing the active medicament, surrounded by a swelling layer without active medicament and then by an external coating which allows release of the active medicament 12 hours after the particles are released from the tablet or capsule.

Figure 4:
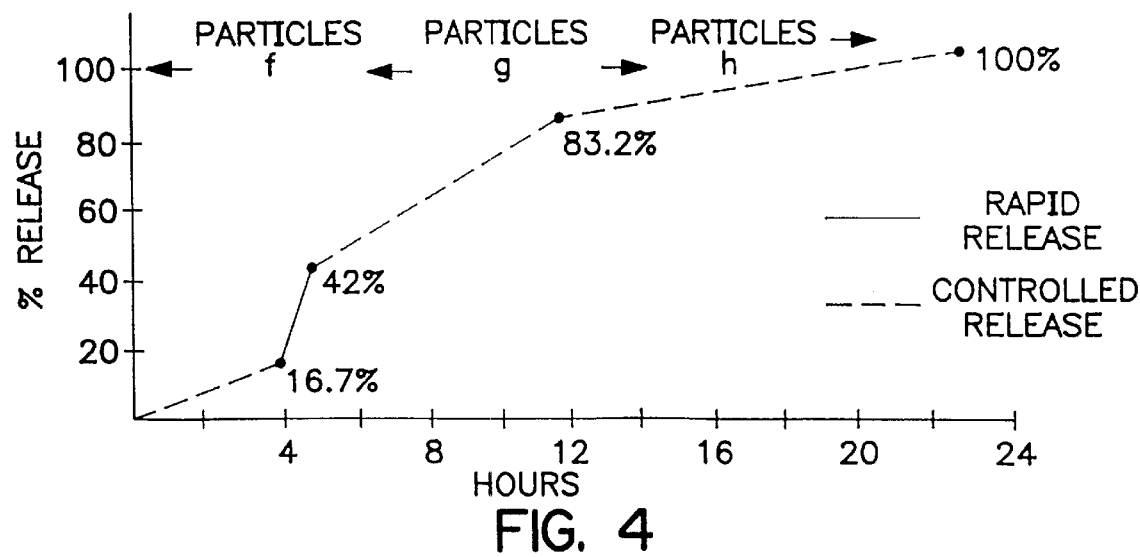
FIG. 4 is a graph showing the release of diltiazem from a drug delivery system consisting of 16.6% dose released from particles of group f between hours 0–4 after dosing, 25% dose from particles of group g between hours 5–6 after dosing, 41.6% dose from particles of group h over hours 6–12 after dosing, and 16.6% dose from in particles of group c between hours 13–24 after dosing (See Example 9).

FIG. 4 is a graph showing the release rate of a drug using the above-described delivery system.

The present invention includes a method for preparing such a pulsatile formulation which comprises forming the core of particles by coating the sugar/starch or cellulose seed or drug crystal with the matrix material of the controlled release layer which comprises a blend of a water-insoluble polyacrylic acid polymer and a water-soluble polymer or monomer, which contains active medicament, or wet granulation of a mixture of a water-insoluble polyacrylic acid polymer of the matrix material of the controlled release layer, and a water-soluble polymer or monomer to which the active medicament has been added.

The coating of the sugar/starch or cellulose seed or drug crystal with a solution or suspension of the matrix material containing the active medicament is continued until the desired thickness of the controlled release layer is obtained. The weight percentage of matrix material in the solvent ranges from 2 to 60% (W/V). In the preferred embodiment, the weight percentage of the matrix material in the solvent ranges form 2 to 50% (W/V).

Wet granulation is accomplished by thoroughly mixing a powder blend of a water-insoluble poly(acrylic acid) polymer of the matrix material with a water-soluble polymer or monomer, to which the active medicament has previously been added. A suitable solvent, either water or organic solvent of high polarity, is used to wet the well-mixed powder, and the wetted mass is then granulated. A mixture of multiple organic solvents or a mixture of water and an organic solvent can also be utilized.

Alternately, the controlled release core can be coated with a swelling agent, in which active medicament is either present or absent.

A still further alternate method of preparation involves the formation of the core of particles by coating the sugar/starch or cellulose seed with the swelling agent with active medicament added.

In a further embodiment the individual particles can be coated with a specific coating layer comprising a major portion of water-insoluble, water-permeable polymer and a minor portion of water-insoluble, water-swellable polymer and water-permeation adjusting agent.

The solvent used in the preparation of the matrix material polymer blend solution or suspension includes, but is not limited to, water and a organic solvent of high polarity, such as ethanol, diethylene glycol, ethylene glycol, and propylene glycol, mixtures of ethanol and ethylene glycol, and mixtures of ethanol and diethylene glycol.

The finished multilayer-core of particles either by coating or granulation has an average diameter of 0.5 to 6 mm, more particularly, 0.8–5 mm diameter.

As utilized herein, the term "active medicament" refers to a drug or other active agent, including, but not limited to small molecule drugs, proteins, peptides and autoantigens, which exert pharmacological actions in the body of a mammal. This active medicament can be a non-protein drug or protein/peptide drugs. Representative bioactive agents which can be utilized in the present invention thus include, but are not limited to, antiarthritis, antacids, anti-gout preparations, antiviral agents, anti-protozoal agents, adrenergic blocking agents, anti-infectives, antihypertensive drugs, analgesics, adrenal cortical steroid inhibitors, anti-inflammatory substances, antiarrhythmics, sedatives, vasodilators, psychotropics, vitamins, cough suppressants, antihistamines, decongestants, anti-obesity drugs, antiemetics, antianginal drugs, vasoconstrictors and migraine treatments, antipyretics, hyper- and hypoglycemic agents, diuretics, anti-nauseants, anticovulsants, mucolytics, neuromuscular drugs, anabolic drugs, antispasmodics, diuretics, antiasthmatics, hormones, and uterine relaxants. Any active medicament which is physically and chemically compatible with water-soluble polymer, of which structural composition has the number ratio of carbon atom to oxygen atom and that of carbon atom to hydroxyl group equal to or less than 1.9: 1 and 5: 1, respectively, and with poly(acrylic acid) polymer may be used in the present invention.

Specific representative bioactive peptides and peptidiomimetics include, but not limited to, TRH, DDAVP, LHRH agonists, LHRH agonists, DADLE, metkephamid, oxytocin, insulin-like growth factors, growth hormone releasing factor, sleep inducing peptide, opiate antagonists, opiate agonists, DGAVP, somatostatin, peptide T, vasoactive intestinal polypeptide, gastric inhibitory peptide, cholecystokin and its active fragments, gastrin releasing peptide, ACTH and its analogues, and enkephalins.

Specific bioactive proteins include, but not limited to, growth hormones, interferons, interleukins, calcitonin, insulin-like growth factors, insulin, colony stimulating factor, tumor inhibitory factors, transforming growth factors, epidermal growth factor, atrial naturetic factor, proinsulin, nerve growth factor, calcitonin, transforming growth factor beta, and glucagon.

Specific representative antigens include, but not limited to, self-antigens and nonself-antigens implicated in autoimmune diseases, and their effective tolerogenic fragments, such as insulin, glutamic acid decarboxylase, heat shock protein 65, bovine serum albumin, carboxypeptidase H, ICA-69, type II collagen and its effective tolerogenic fragments, myelin basic protein and its effective tolerogenic fragments, and many others implicated in autoimmune diseases. The autoimmune diseases include, but not limited to, systemic lupus erythematosus, dermatomyositis, Sydenham's chorea, rheumatoid arthritis, rheumatic fever, thrombocytopenic purpura, polyglandular syndromes, bullous pemphigoid, diabetes mellitus, henoch-schonlein purpura, post-streptococcal nephritis, systemic lupus erythematosus, erythema nodosum, Takayasu's arteritis, myasthenia gravis, thrombocytopenic purpura, Addison's disease, rheumatoid arthritis, multiple sclerosis, sarcoidosis, ulcerative colitis, erythema multiform, IgA nephropathy, polyarteritis nodosa, ankylosing spondylitis, goodpasture's syndrome, thromboangiitis obliterans, Sjogren's syndrome, primary biliary cirrhosis, thyrotoxicosis, scleroderma, chronic active hepatitis, polymyositis/dermatomyositis, polychondritis, pemphigus vulgaris, Wegener's granulomatosis, Henoch-Schonlein purpura, membranous nephropathy, amyotrophic lateral sclerosis, tabes forsalls, giant cell arteritis/polymyalgia, pernicious anemia, bullous pemphigoid, rapidly progressive glomerulonephritis, myasthenia gravis and fibrosing alveolitis.

The mild reaction conditions utilized in the preparation of the composition of the instant invention provide a facile and easy formulation which is especially suitable for bioactive agents which can be denatured by the use of heat or organic solvents. Thus, the present invention finds particular utility in the formulation of proteins, peptides and antigens, where conditions varying from physiological conditions can cause a partial, if not total loss of bioactivity.

The weight percentage of the active medicament loaded into the controlled release layer of the present invention ranges from 1 to 60% with the total weight of polymer blend, active medicament and other excipients, such as plasticizers, being 100%. The weight percentage of drug loading depends upon the particular active medicament, and the desired dose to be administered within the time period.

To prepare the polymer blend based controlled release matrix utilized as the controlled release layer of the instant invention, the poly(acrylic acid) polymer and the water-soluble polymer or monomer are mixed in water or in an organic solvent of high polarity at the desired concentration in the range of about 0.05 to about 50% by weight, and then the active medicament is added. The amount ratio of poly(acrylic acid) to the water-soluble polymer or monomer preferably range from 1:40 to 40:1, depending on the desired release pattern of the active medicament.

The invention will be further illustrated by the following Examples, which are to be considered illustrative of the invention, and not limited to the precise embodiments shown.

EXAMPLE 1
Carbopol 971P and carboxymethyl cellulose blend for controlled release layer With the amount ratio of both polymers being 1: 1, the aqueous concentrations of Carbopol 971P and carboxymethyl cellulose range from 0.5% (W/V) to 1.5% (W/V). When ethanol is used, the respective concentrations range from 1% (W/V) to 20% (W/V). For the amount ratio of Carbopol 971P : carboxymethyl cellulose being 1:4, the aqueous concentrations of Carbopol 971P and carboxymethyl cellulose range from 0.2% (W/V) and 0.8% (W/V), respectively, to 1.5% (W/V) and 6% (W/V), respectively. When ethanol is used, the respective concentrations range from 1% (W/V) and 4% (W/V) to 5% (W/V) and 20% (W/V). After dispersing both polymers and the active medicament in water or ethanol, a homogeneous polymer solution or suspension is obtained by slow stirring. The solution is then used for coating of a starch/sugar seed.

EXAMPLE 2
Carbopol 971P and hydroxyethyl cellulose blend

With the amount ratio being 1:1, the aqueous concentrations of Carbopol 971P and hydroxyethyl cellulose range from 0.5% (W/V) to 1.5% (W/V). When ethanol is used, the respective concentrations range from 1% (W/V) to 20% (W/V). For the mount ratio of Carbopol 971P: hydroxyethyl cellulose being 1:4, the aqueous concentrations of Carbopol 971P and hydroxyethyl cellulose range from 0.2% (W/V) and 0.8% (W/V), respectively, to 1.5% (W/V) and 6% (W/V), respectively. When ethanol is used, the respective concentrations range from 1% (W/V) and 4% (W/V) to 5% (W/V) and 20% (W/V). Substantial repetition of procedures are described in Example 1 affords a controlled release matrix.

EXAMPLE 3
Carbopol 971P and propylene glycol alginate blend

With the amount ratio being 1:1, the aqueous concentrations of Carbopol 971P and propylene glycol alginate range from 0.5% (W/V) to 1.5% (W/V). When ethanol is used, the respective concentrations range from 1% (W/V) to 20% (W/V). For the amount ratio of Carbopol 971P: propylene glycol alginate being 1:4, the aqueous concentrations of Carbopol 971P and propylene glycol alginate range from 0.2% (W/V) and 0.8% (W/V), respectively, to 1.5% (W/V) and 6% (W/V), respectively. When ethanol is used, the respective concentrations range from 1% (W/V) and 4% (W/V) to 5% (W/V) and 20% (W/V). Substantial repetition of the procedures described in Example 1 affords a controlled release matrix layer.

EXAMPLE 4
Carbopol 971P and D-mannitol blend

With the amount ratio being 1:1, the aqueous concentrations of Carbopol 971P and D-mannitol range from 0.5% (W/V) to 1.5% (W/V). When ethanol is used, the respective concentrations range from 1% (W/V) to 20% (W/V). For the amount ratio of Carbopol 971P: D-mannitol being 1:4, the aqueous concentrations of Carbopol 971P and D-mannitol range from 0.2% (W/V) and 0.8% (W/V), respectively, to 1.5% (W/V) and 6% (W/V), respectively. When ethanol is used, the respective concentrations range from 1% (WI/V) and 4% (W/V) to 5% (W/V) and 20% (WIV). Substantial repetition of the procedures described in Example 1 affords a controlled release matrix layer.

EXAMPLE 5
Carbopol 971P and Xylitol blend

With the amount ratio being 1:1, the aqueous concentrations of Carbopol 971P and xylitol range from 0.5% (W/V) to 1.5% (W/V). When ethanol is used, the respective concentrations range from 1% (W/V) to 20% (W/V). For the amount ratio of Carbopol 971P: D-mannitol being 1:4, the aqueous concentrations of Carbopol 971P and D-mannitol range from 0.2% (W/V) and 0.8% (W/V), respectively, to 1.5% (W/V) and 6% (W/V), respectively. When ethanol is used, the respective concentrations range from 1% (W/V) and 4% (W/V) to 5% (W/V) and 20% (W/V). Substantial repetition of the procedures described in Example 1 affords a controlled release matrix layer.

EXAMPLE 6

A delivery system for nifedipine is prepared as follows:
Group A particles are prepared with an inner core consisting of:

| Inner Controlled release layer | |
|---|---|
| Nifedipine | 470 mg |
| Carbopol 971 P | 600 mg |
| Hydroxyethylcellulose | 600 mg |
| Triacetin | 20 mg |
| Sugar/starch seed | 300 mg |

-continued

| Outer Swelling (Rapid Release) layer | |
|---|---|
| Nifedipine | 230 mg |
| Starch glycolate | 200 mg |
| Sodium carboxymethylcellulose | 200 mg | and coated with a coating layer and comprising the following composition until the desired coating thickness is reached:

| Coating layer | |
|---|---|
| Ethylcellulose | 80 g |
| Carbopol 971P | 4 g |
| Montana Talc (hydrophobic in nature) | 2 g |
| Ethanol | 1300 g |

Group B particles are prepared as follows:

| Inner Controlled release layer | |
|---|---|
| Nifedipine | 700 mg |
| Carbopol 971 P | 800 mg |
| Hydroxyethylcellulose | 800 mg |
| Triacetin | 30 mg |
| Sugar/starch seed | 1010 mg |

| Outer Swelling (rapid release) layer | |
|---|---|
| Starch glycolate | 400 mg | and coated with a coating layer comprising the following compositions until the coating thickness is desired:

| Coating layer | |
|---|---|
| Ethylcellulose | 60 g |
| Carbopol 971P | 2 g |
| Montana talc (hydrophobic in nature) | 4 g |
| Ethanol | 1000 g |

Each group of particles were prepared by spray-coating the sugar/starch seed with a blend of the inner controlled release layer components (prepared by the detailed procedures of Examples 1–5) and then by that of the swelling (rapid release) layer components using water or ethanol or other solvents of high polarity and the air suspension technique known as "Wurster" coating in a fluidized bed. Typically, the drying temperature ranges from 40° C. to 120° C., and, most preferably, from 40° C. to 80° C. When using ethanol or another solvent of high polarity, or a mixture of organic solvents of high polarity, 5 parts of organic solvent is used with 1 part of solid mixed components of either the inner controlled-release layer or swelling layer. Alternatively, water can replace ethanol as the solvent with 100 parts of water being utilized with 1 part of solid mixed components of the inner controlled-release layer and 20 parts of water being utilized with 1 part of solid mixed components of swelling layer.

Alternatively, each group of particles can be prepared by granulation. The solid mixture for the controlled-release layer is mixed in a Hobart blender and milled through a 50-mesh screen. Ethanol is then gradually added with 0.2 ml for a gram of powder mixture. The wet granulation is then passed through a 20-mesh screen and dried at 80° C.

For the external coating layer, ethanol is used as the solvent with 15 ml of ethanol for 1 g of solid mixed components of external coating.

The external coating of the group A particles continues until the lag time is 0.5 hr. The external coating layer of the group B particles continues until the lag time is 12 hours. 5% by weight of the group A particles are mixed with 5% by weight of group B particles and then formulated in a capsule of approximately 330 mg.

Alternatively, these particles can be mixed with 50 mg of pharmaceutical grade binder, lubricant, and disintegrant to form a tablet of 380 mg.

In the dissolution test with the method described in U.S. Pharmacopoeia XXII (Paddle Method), the results show a dissolution profile of 14% released by 1 hour, 50% by 12 hours, and 100% by 21 hours.

EXAMPLE 7

A delivery system for potassium chloride is prepared as follows:

| Inner core | |
|---|---|
| Potassium chloride | 72% |

| Controlled release layer | |
|---|---|
| Pulverized potassium chloride | 10% |
| Carbopol 971 P | 8% |
| Hydroxyethylcellulose | 8% |
| Triethyl citrate | 0.04% | and coating with a coating layer of

| Coating layer | |
|---|---|
| Ethylcellulose | 1.6% |
| Carbopol 971P | 0.16% |
| Magnesium stearate | 0.08% |

These particles were prepared by passing potassium chloride crystal through the 30 mesh screen and then spray-coating potassium chloride crystals with the mixture of the inner controlled release layer components, using the air suspension technique known as "Wurster" coating in a fluidized bed. Typically, the drying temperature ranges from 40° C. to 120° C., most preferably, from 40° C. to 80° C. When ethanol is used, 5 parts of ethanol is for 1 part of solid mixed components of inner controlled-release layer or rapid release layer or swelling layer. Alternatively, water can replace ethanol as the solvent with 100 parts of water for 1 part of solid mixed components of inner controlled-release layer and 20 parts of water for 1 part of solid mixed components of swelling layer.

The potassium chloride crystals are separated into three groups, with each group coated with the same amount of the components of the controlled-release layer but with progressively thicker external coating thickness layers so that the timed release of the individual groups of particles are separated by an interval of 8 hours. For the external coating, ethanol is used as the solvent with 15 parts of ethanol for 1 part of solid mixed components of external coating. These particles can be formulated in capsules. Alternatively, these particles can be mixed with pharmaceutical grade binder, lubricant, and disintegrant to form a tablet of 1,500 mg or 750 mg.

In the dissolution test with the method described in U.S. Pharmacopoeia XXII (Paddle Method), the results show a dissolution profile of a 33% released by 8 hours, 66% by 16 hours, and 99% by 24 hours.

This delivery system delivers three sequential pulse dosages with each one being a controlled-release pulse over 8 hours. By slowly releasing potassium chloride in the gastrointestinal tract, this system prevents localized high concentrations of potassium chloride and consequently prevents irritation to the gastrointestinal mucosal tissues. Further, the plasticized controlled release layer also serve as a thick cushion between the potassium chloride crystal and the external coating, thereby preventing the sharp edge of crystal breaking the coating membrane during tablet compression.

EXAMPLE 8

A drug delivery system for potassium chloride is prepared as follows:

| Inner Crystal core | |
| --- | --- |
| Potassium chloride | 82% |
| Controlled release layer | |
| Carbopol 971 P | 8% |
| Hydroxyethylcellulose | 8% |
| Triethyl citrate | 0.04% |
| External coating layer | |
| Ethylcellulose | 1.6% |
| Carbopol 971P | 0.16% |
| Magnesium stearate | 0.08% |

The method of preparation is as prepared as described in Example 7.

EXAMPLE 9

A drug delivery system for dialtiazem is prepared as follows:
Group 1 Particles are prepared as follows:

| Inner controlled release core | |
| --- | --- |
| Dialtiazem | 80 g |
| Carbopol 971P | 30 g |
| Dextran | 30 g |
| Starch/sugar seed | 160 g |
| Swelling layer | |
| Starch glycolate | 100 g |
| External coating layer | |
| Ethylcellulose | 20 g |
| Carbopol 971P | 1 g |
| Montana Talc (hydrophobic in nature) | 0.5 g |

Group 2 Particles are prepared as follows:

| Inner controlled release core | |
| --- | --- |
| Dialtiazem | 100 g |
| Carbopol 971P | 38 g |
| Dextran | 38 g |
| Starch/sugar seed | 200 g |
| Immediate rapid release layer | |
| Starch glycolate | 60 g |
| Dialtiazem | 60 g |
| External coating layer | |
| ethylcellulose | 20 g |
| Carbopol 971P | 2 g |
| Montana Talc (hydrophobic in nature) | 0.5 g |

Group 3 Particles are prepared as follows:

| Inner controlled release core | |
| --- | --- |
| Dialtiazem | 80 g |
| Carbopol 971P | 40 g |
| Dextran | 40 g |
| Starch/sugar seed | 160 g |
| Rapid release layer | |
| Starch glycolate | 100 g |
| External coating layer | |
| Ethylcellulose | 20 g |
| Carbopol 971P | 1 g |
| Montana Talc (hydrophobic in nature) | 1 g |

These particles were prepared by spray-coating the sugar/starch seed with the mixture of components for the inner controlled release layer or for the rapid release layer using ethanol and the air suspension technique known as "Wurster" coating in a fluidized bed. The drying temperature ranges from 40° C. to 120° C., most preferably, from 40° C. to 80° C. When ethanol is used, 5 parts of ethanol is used for 1 part of solid mixed components of either inner controlled-release layer or swelling layer. Alternatively, water can replace ethanol as the solvent with 100 parts of water for 1 part of solid mixed components of inner controlled-release layer and 20 parts of water for 1 part of solid mixed components of swelling layer.

Alternatively, the particles can be prepared by the granulation method. The solid mixture for the controlled-release layer is mixed in a Hobart blender and milled through a 50-mesh screen. Ethanol is then gradually added with 0.2 ml for a gram of powder mixture. The wet granulation is then passed through a 20-mesh screen and dried at 80° C.

For the external coating, ethanol is used as the solvent with 15 ml of ethanol for 1 g of solid mixed components of external coating. The external coating of the group 1 particles is adjusted so that the release of the active medicament is instant. The external coating of the group 2 particles is continued until the lag time for release of the active medicament is 4 hours. The external coating of the group 3 particles is continued until the lag time for release of the active medicament is 12 hours. 0.05% by weight of the group 1 particles are mixed with 0.1% by weight of the group 2 particles and 0.05% by weight of group 3 particles, and the resultant mixture is then formulated in a capsule of approximately 900 mg. Alternatively, these particles can be mixed with 50 mg of pharmaceutical grade binder, lubricant, and disintegrant to form a tablet of 950 mg.

In the dissolution test with the method described in U.S. Pharmacopoeia XXII (Paddle Method), the results show a dissolution profile of a 16.5% dialtiazem released by 4 hours, 41.6% of dialtiazem released by 6 hours, 75% of the dialtiazem released by 12 hours, and 100% of the dialtiazem released by 24 hours.

The invention is described above in detail with reference to the preferred embodiments. Variations resulting from modifications are within the scope of the invention.

What is claimed is:

1. A pulsatile drug delivery system for the release of an active medicament in pulsed dosages when exposed to an aqueous environment which comprises one or more groups of particles which contain the active medicament, enclosed in a solid dosage form, with each of said groups having a distinct pattern of drug release based upon its combination of controlled release layers, swelling layers, and coating layers, wherein the controlled release layer of the particles comprises a matrix comprising a slightly cross-linked poly (acrylic acid) polymer of an approximate molecular weight of 250,000 to above 4 billion and a water-soluble polymer or monomer in a weight ratio ranging from 40:1 to 1:40.

2. A system according to claim 1 wherein the active medicament is a protein, peptide or autoantigen or non-protein drugs.

3. A system according to claim 1 wherein the weight ratio of the poly(acrylic acid) polymer to the water soluble polymer or monomer in the controlled release layer is 10:1 to 1:10.

4. A system according to claim 1 wherein the water-soluble polymer or monomer has a carbon-oxygen ratio being less than or equal to 1.9: 1 and is selected from the group consisting of sodium carboxymethyl cellulose, hydroxyethyl cellulose, hydroxypropyl cellulose, propylene glycol alginate, sodium alginate, dextran, alginic acid, carboxymethylcellulose, D-mannitol and xylitol.

5. A system according to claim 1 further comprising a plasticizer in the controlled release layer in an amount of about 1–20% by weight of the total composition.

6. A system according to claim 5 wherein the plasticizer is selected from the group consisting of propylene glycol, triethylcitrate, sorbitol, triacetin, dimethyl phthalate, diethyl phthalate, dibutyl phthalate, dihexyl phthalate, butyl octyl phthalate, dibutyl sebacate, polyhydric alcohols, glycerides, castor oil, propylene glycol, glycerol triacetate, triethyl citrate, polyethylene glycol, glycerol, dioctyl azelate, epoxidized tallate, triisoctyl trimellitate, triisononyl trimellitate, sucrose acetate isobutyrate, epoxidized soybean oil, and acetylated monoglycerides.

7. A system according to claim 1 wherein the particles are formulated into tablets or capsules using standard pharmaceutical procedures, optionally using additional inactive pharmaceutical excipients.

8. A system according to claim 7 wherein the active medicament is a protein, peptide or autoantigen or non-protein drugs.

9. The system of claim 1 wherein said groups of particle units contain the same active medicament.

10. The system of claim 1 wherein said controlled release layer and swelling layer contain different active medicaments.

11. The system of claim 1 wherein said coating layer comprises of a major portion of water-insoluble, water-permeable polymer;

a minor portion of water-insoluble, water-swellable polymer; and water-permeation adjusting agent, either hydrophobic or hydrophilic in nature.

12. The system of claim 1 wherein the swelling layer consists of a swelling agent with an active medicament.

13. The system according to claim 1 wherein the swelling layer comprises a water-insoluble, water-swelling polymer selected from the group consisting of hydroxypropylcellulose, cross-linked polyvinylpyrrolidone, cross-linked carboxymethylcellulose, pregelatinized starch, sodium starch glycolate, polyvinyl acetate, polyacrylic acid, acrylate-co-polymer, carboxymethylcellulose calcium, carboxymethylcellulose sodium, poly(hydroxyethyl-methacrylate), poly(methacrylic acid), poly(acrylamide), sodium starch glycolate, starch, poly(hydroxyalkyl methacrylate) with a molecular weight of 32,000 to 5,500,000, poly(electrolyte) complexes, poly(vinyl alcohol), acrylate polymers with water absorbability of roughly 400 times its original weight, a mixture of poly(vinyl alcohol) and poly(N-vinyl-2-pyrrolidone), poly(acrylic acid) with a molecular weight of 80,000 to 200,000, polyoxy polyethylene oxide polymers with a molecular weight of 100,000 to 5,000,000, polysaccharides, agar, acacia, karaya, tragacanth and algins, pectin with a molecular weight of 30,000 to 300,000, and polyoxybutylenepolyethylene block polymer.

14. The system of claim 11 wherein the water-insoluble, water-permeable polymer is selected from the group consisting of cellulose acylate, cellulose acetate, cellulose diacylate, cellulose diacetate, cellulose triacylate, cellulose triacetate, mono-, di-, and tri-cellulose alkanylate, mono-, di- and tri-alkenylates, mono-, di- and tri-aroylates, cellulose trivalerate, cellulose trilaurate, cellulose tripalmitate, cellulose trioctanoate, cellulose tripropionate, cellulose diesters, cellulose disuccinate, cellulose dipalmitate, cellulose dioctanoate, cellulose dicarpylate, cellulose actate heptonate, cellulose valerate palmitate, cellulose acetate octonoate, cellulose propionate succinate, cellulose acetate valerate, cellulose acetaldehyde, dimethyl cellulose acetate, cellulose acetate ethylcarbamate, hydroxypropylmethylcellulose, semipermeable polyamylsulfanes, semipermeable urethane, cellulose acetate methylcarbamate, cellulose dimethylaminoacetate, semipermeable sulfonated polystyrenes, semipermeable silicone rubbers, semipermeable styrenes, sulfonated polystyrenes, polyurethanes, polydiethylaminomethylstyrene, cellulose acetate methylcarbamate, ethylcellulose, shellac, polymethylstyrene, polyvinylacetate, seimpermeble (polysodium styrenesulfonate), and semipermeable poly (vinylbenzymtrimethylammonium chloride.

15. The system of claim 11 wherein the water-insoluble, water-swellable polymer is selected from the group consisting of hydroxypropylcellulose, cross-linked polyvinylpyrrolidone, cross-linked carboxymethylcellulose, pregelatinized starch, sodium starch glycolate, polyvinyl acetate, polyacrylic acid, acrylate-co-polymer, carboxymethylcellulose calcium, carboxymethylcellulose sodium, poly(hydroxyethyl-methacrylate), polymethacrylic acid), poly(acrylamide), sodium starch glycolate, starch, poly (hydroxyalkyl methacrylate) with a molecular weight of 32,000 to 5,500,000, poly(electrolyte) complexes, poly (vinyl alcohol), acrylate polymers with water absorbability of roughly 400 times its original weight, a mixture of poly(vinyl alcohol) and poly(N-vinyl-2-pyrrolidone), poly (acrylic acid) with a moleculare weight of 80,000 to 200, 000, Polyoxy polyethylene oxide polymers with a molecular weight of 100,000 to 5,000,000, polysaccharides, agar, acacia, karaya, tragacanth and algins, pectin with a molecular weight of 30,000 to 300,000, and polyoxybutylene-polyethylene block polymer.

16. The system of claim 11 wherein the water permeation-reducing agents are selected from the group consisting of fatty acids, metal salts of fatty acids and talc.

17. A system according to claim 7 wherein the excipients comprise binders, diluents and/or disintegrants.

* * * * *